(12) United States Patent
Mohl et al.

(10) Patent No.: US 9,345,824 B2
(45) Date of Patent: May 24, 2016

(54) VENTRICULAR ASSIST DEVICE

(71) Applicants: Technische Universität Wien, Vienna (AT); Werner Mohl, Altenmarkt/Thennenberg (AT)

(72) Inventors: Werner Mohl, Altenmarkt/Thennenberg (AT); Margit Gföhler, Vienna (AT); Christoph Janeczek, Felixdorf (AT); Reinhard Willinger, Vienna (AT)

(73) Assignee: ASSISTOCOR GMBH & CO KG, Vienna (AT)

( * ) Notice: Subject to any disclaimer, the term of this patent is extended or adjusted under 35 U.S.C. 154(b) by 25 days.

(21) Appl. No.: 14/324,727

(22) Filed: Jul. 7, 2014

(65) Prior Publication Data
US 2016/0000983 A1    Jan. 7, 2016

(51) Int. Cl.
*A61M 1/10*    (2006.01)
*A61M 1/12*    (2006.01)

(52) U.S. Cl.
CPC ............ *A61M 1/1086* (2013.01); *A61M 1/1005* (2014.02); *A61M 1/122* (2014.02); *A61M 1/127* (2013.01)

(58) Field of Classification Search
CPC .... A61M 1/1086; A61M 1/127; A61M 1/122
See application file for complete search history.

(56) References Cited

U.S. PATENT DOCUMENTS

| 2002/0173693 | A1* | 11/2002 | Landesberg | ........ A61M 1/1046 600/16 |
| 2005/0107657 | A1* | 5/2005 | Carrier | .................. A61M 1/101 600/16 |
| 2009/0203957 | A1 | 8/2009 | LaRose et al. | |
| 2011/0178361 | A1 | 7/2011 | Yomtov | |

FOREIGN PATENT DOCUMENTS

| WO | 2009/099644 A1 | 8/2009 |
| WO | 2011/092394 A1 | 8/2011 |

OTHER PUBLICATIONS

Partial International Search Report for PCT/IB2015/001086 mailed Oct. 9, 2015 (7 pages).

* cited by examiner

*Primary Examiner* — Rex R Holmes
(74) *Attorney, Agent, or Firm* — Fitch, Even, Tabin & Flannery LLP

(57) ABSTRACT

The invention relates to a ventricular assist device for intraventricular placement inside a human heart including an anchor element configured to be mounted to the heart in the region of the apex; and a pump connected to the anchor element comprising a preferably tubular housing having an intraventricular inlet and an intraventricular outlet and further comprising a drive for driving a rotor arranged within the housing, thereby providing pulsatile flow acceleration in the left ventricle synchronized with the heart beat and according to volume requirements in the left ventricle.

10 Claims, 8 Drawing Sheets

VENTRICULAR ASSIST DEVICE

FIELD

Figure 1:
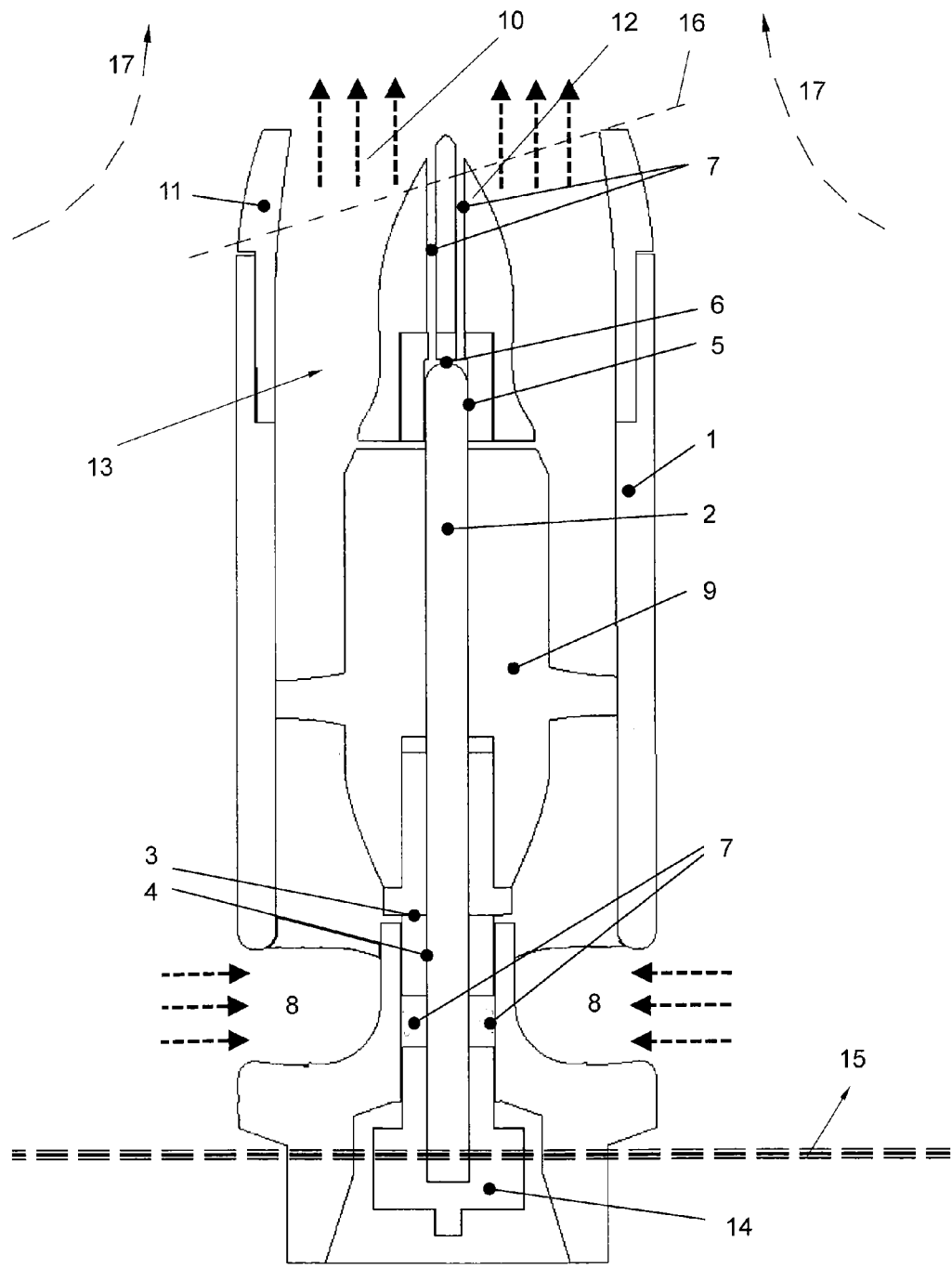

The invention refers to a ventricular assist device for intraventricular placement to accelerate blood flow inside a human heart thereby enhancing the ejecting volume, comprising an anchor element configured to be mounted to the heart in the region of the apex and a pump connected to the anchor element and comprising a preferably tubular housing having an inlet and an outlet and further comprising a drive for driving a rotor arranged within the housing and a special adjustable nozzle directing the ejecting blood flow.

BACKGROUND

Left ventricular contractility normally accelerates blood within the left ventricle and ejects as an average 70% of the blood volume contained in the left ventricle into the circulatory system. In case of severe heart failure this mechanism is insufficient and the majority of the blood volume remains within the ventricle, thus producing inadequate cardiac output.

Several systems are known to correct cardiac failure bypassing the left ventricle and continuously ejecting the blood from the left ventricle via an artificial conduit directly into the great thoracic arteries. Such systems operate as left ventricular assist devices (LVAD) in order to help the heart's weakened left ventricle pump blood throughout the body.

The LVAD can be used as a bridge-to-transplant, which means it can help a patient survive until a donor heart becomes available for transplant. This option may be appropriate for people whose medical therapy has failed acutely and/or who are hospitalized with end-stage systolic heart failure. The LVAD also can be used as destination therapy, which is an alternative to heart transplantation. Destination therapy provides long-term support in patients who are not candidates for transplant, because of severe comorbidities and especially of older age. When used as a bridge-to-transplant or as destination therapy, the LVAD provides effective chronic hemodynamic support, maintains or improves other organ function, improves exercise performance and enables participation in cardiac rehabilitation.

These assist devices comprise a continuous flow pump, which produces a continuous, non-pulsatile flow of blood through the circulatory system using a rotary pumping mechanism. There is, however, a multitude of side effects on end organs as well as major cardiac surgery for implantation. Recently several minimal invasive forms of cardiac assist devices have been developed. WO 2009/099644 A1 discloses a ventricular assist device for intraventricular placement inside a human heart. It comprises a pump that is implanted within the left ventricle with the outflow cannula projecting through the aortic valve and terminating short of the aortic arch. The pump is fixed to the wall of the heart near the apex by means of an anchor element in order to hold the pump and the outflow cannula in position. The device disclosed in WO 2009/099644 A1 produces a continuous flow of blood, wherein the aortic valve is penetrated by the outflow cannula and is therefore unable to close effectively, but cooperates with the pump traversing it in order to prevent retrograde flow of blood into the left ventricle during diastole. Because of the continuous character of the flow the valve is held in only one position, which increases the risk of valve thrombosis and/or significant retrograde leakage into the failing and assisted ventricle.

The drawback of the device disclosed in WO 2009/099644 A1 and of other continuous flow ventricular assist devices is that—since they have to maintain up to 100% of cardiac output—they are disturbing normal end organ function and contractile pattern of the diseased heart, leaving nutritive coronary blood flow unchanged and therefore limit structural recovery.

SUMMARY

Therefore, it is an object of the instant invention to provide an improved ventricular assist device for intraventricular placement inside a human heart. In particular, it is an object of the invention to optimize blood flow and support residual contractility without the severe side effects of continuous flow as mentioned above. In particular, it is an object of the invention to provide an implant that does not involve the risk of impairing the remaining contractile force of the failing ventricle.

Further, it is an object of the invention to avoid the drawbacks associated with LVAD systems having extraventricular conduits. In available LVAD systems with external conduits the aortic valve remains closed, because all ejecting blood is bypassed. Therefore, the system is limited only to patients without a structural insufficient aortic valve.

It is a further object of the invention to provide an assist device that can be easily deployed to the heart without a sternotomy.

It is a further object of the invention to provide a closed loop between the circulatory demand, the remaining force of the diseased ventricle and the supporting pump.

The words "proximal" and "distal" are used herein to denote directions and ends of the device in relation to blood flow. As used herein, when referring to the ventricular assist device, the term "proximal" refers also to the directions toward the physiologic blood flow and surgeon or other operating room personnel during installation of the device and the term "distal" has the opposite meaning.

The invention generally provides an improved ventricular assist device for intraventricular placement (inside a human heart) providing pulsatile flow acceleration in the left ventricle, preferably during systole. Preferably, the pulsatile flow acceleration is synchronized with the heartbeat.

In some embodiments, the invention provides ventricular assist device comprising an anchor element configured to be mounted to the heart in the region of the apex and a pump connected to the anchor element and comprising a preferably tubular housing having an inlet and an outlet, said inlet and said outlet being arranged within the ventricle, and further comprising a drive for driving a rotor arranged within the housing. Preferably, the drive is an electric or pneumatic motor.

In some embodiments, in order to provide pulsatile flow acceleration during systole, the invention provides a control unit connected with the drive for controlling the pump, said control unit comprising a first sensor for sensing a heartbeat of the heart and configured to control the pump to be driven in a pulsatile manner in synchronization with the heartbeats.

The invention is based on the idea to correct left ventricular failure by increasing the velocity of the blood column during the ejecting period of the heart (i.e. during cardiac systole) and redirecting blood flow within the ventricle towards the aortic valve. Normally, blood entering the left ventricle via the mitral valve swirls in a vortex near the apex and gets accelerated during the ejection period. In case of heart failure the heart does not provide enough acceleration of ventricular blood flow, thereby forming a second vortex in the mid cavity without producing sufficient force to eject blood. The inventive device assists the heart by providing a flow accelerator within the ventricle. Thus, the inventive approach uses a different pathophysiologic concept than disclosed in WO 2009/099644 A1. Instead of sucking the blood out of the ventricle continuously and directly delivering the pumped blood to the aorta, the invention just assists the heart in its natural way of functioning.

Further, the invention does neither traverse nor bridge the aortic valve, but uses the aortic valve as in an unassisted, healthy heart.

Further, the device does not provide continuous blood flow, but pulsatile blood flow. Pulsatile flow is a flow with periodic variations, like the flow in the cardiovascular system. By synchronizing the pulsatile flow provided by the pump of the assist device with the heartbeat, the periodic variations of the flow produced by the assist device preferably are substantially in phase with the periodic variations of the flow in the cardiovascular system, in particular at the beginning of the aorta.

Preferably, the assist device produces a pulsatile flow by causing alternating phases of no pumping action and of pumping action. Alternatively, the assist device produces a pulsatile flow by causing alternating phases of low pumping action and of enforced pumping action. Thus, the control unit of the assist device is configured to alternately turn on and turn off the pump in order to produce periodic variations of the blood flow within the pump housing. Preferably, the pumping action is triggered only during the early phase of systole until peak pressures are reached within the aorta. Preferably the pump action is initiated by applying a ramp function thereby accelerating the rotor and then leaves the rotor fading out according to the blood volume sensed in the heart at late diastole.

The assist device of the invention is configured to be implanted into the apical region of the heart.

According to a preferred embodiment of the invention, the pump is configured as an axial-flow pump in order to pump blood from the inlet of the pump housing to the outlet.

In order to increase the effect of flow acceleration within the ventricle, the device is preferably configured to additionally operate as an injector so as to entrain blood from within the ventricle downstream of said pump rotor, namely entraining blood that is outside of and preferably distal to the pump housing. Preferably, the injector effect of the assist device is achieved by the blood flow produced by the rotor between the inlet and the outlet of the pump housing, which blood flow entrains additional blood from within the ventricle to the aortic valve. In order to allow for said entraining of additional blood, the pump housing preferably comprises at least one additional inlet opening downstream of the rotor.

The injector effect of the pump may preferably also be achieved by beveling the outlet opening of the pump housing so as to obtain an end face that is inclined relative to the axis of the pump.

Preferably, the flow cross-section of the pump continuously decreases in a flow direction at the outflow end of the pump housing so as to form a nozzle. Preferably, the nozzle is able to direct the flow towards the aortic valve and to entrain surrounding blood by sucking it into the nozzle through at least one lateral opening. The nozzle enhances the injector effect of the pump.

Preferably, the nozzle comprises guide plates extending in the axial direction of the pump so as to redirect rotating blood flow exiting the impeller to induce an axially directed laminar blood flow.

Preferably, the end region of the pump housing, downstream of the rotor, is configured to allow for an adjustment of the outflow direction of the pumped blood. In particular, the end region of the pump housing may be flexible to optimize the flow direction towards the outflow of the heart so as to prevent jet-induced lesions on the myocardium. In this way, the flow of blood exiting the pump housing via the outlet opening can be directed to the aortic valve and then fixed in the adjusted position. Preferably, the adjustment of the outflow direction of the pump is feasible in the implanted state of the device.

Preferably, the adjustable end region of the pump housing cooperates with an actuator in order to adjust the outflow direction of the pump. The actuator may be realized by an electric motor and may be positioned outside of the heart. When positioned outside of the heart, the actuator is preferably connected to the adjustable end region of the pump housing by means of suitable connecting means, such as a steering wire. The adjusting movement of the adjustable end region of the pump housing as induced by the actuator is preferably controlled under the guidance of a blood flow monitoring technique. Preferably, the actuator is controlled by a continuous flow sensor incorporated into the adjustable end region so as to position the adjustable end region of the pump housing into the optimal position within the outflow tract. Periodic monitoring of the orientation of the adjustable end region of the housing is advantageous for an optimal ejection of blood from the failing heart into the aorta, since the heart remodels during therapy.

Preferably, the outflow orientation of the pump is adjusted automatically, by using a control algorithm, in particular a closed loop controller. Preferably, the outflow direction of the pump is controlled as a function of the blood flow speed measured in the vicinity of the outflow end of the pump. The blood flow speed is indicative of whether the blood flow is directed to the aortic valve or whether the blood flow induced by the pump is reflected at the heart wall surrounding the aortic valve or into the inflow region. The flow speed may be measured by means of an ultrasonic Doppler sensor that is mounted at the outflow end of the pump. Preferably, the further parameters to be considered in the control algorithm are at least one of hemodynamic variables such as hemodynamic pressure, pump speed, energy consumption and hemodynamic pressure.

According to another preferred embodiment, the pump comprises a magnetic coupling for coupling a drive, in particular a rotary drive, to the rotor. The magnetic coupling provides a non-contact and wearless transmission of the rotary motion of the drive to the rotor. Further, the magnetic coupling facilitates the removal of the drive and the mounting of a new drive if needed.

Preferably, the drive is an electric motor. Alternatively, the drive may be configured as a pneumatic drive, so that the rotor of the pump is driven by pneumatic force. Preferably, the pneumatic drive is located outside the heart, wherein the magnetic coupling allows a complete separation between the drive and the pump rotor. In this embodiment the pneumatic energy is delivered by a percutaneous tube connected with a pneumatic source delivering pulsed volume flows into the turbine positioned outside of the heart, which is magnetically coupled to the blood pumping impeller.

Preferably, the drive is at least partially arranged proximally of the anchor element so as to be placed at least partially outside of the heart when in use. In particular, the entire drive is arranged outside of the heart when in use. In case of an electric motor, this helps to keep away the heat generated by the electric motor from the ventricle and the blood contained therein so as to reduce the risk of a thrombosis.

Alternatively, the motor may be positioned intraventricularly. Preferably, the pump rotor may be directly coupled to the rotor of the electric motor, wherein the rotor is supported within the motor by means of a contactless magnetic bearing. In this way, the magnetic bearing provides for an annular clearance between the rotor and the stator of the electric motor, the clearance establishing a flow cross-section for the blood pumped by the pump rotor. Reference is made to U.S. Pat. No. 3,436,570.

According to another preferred embodiment, the pump output of the pump, i.e. the rotational speed of the pump rotor, and/or the activation time period of the pump are adjusted depending on the patient's level of activity and need of support. Preferably, the control unit is configured to control the rotational speed of the pump rotor as a function of heart rate signals derived from the first sensor. In particular, the rotational speed of the pump rotor is increased with increasing heart rate in order to compensate for the reduction of the ejection period.

Further, the rotational speed of the pump rotor is decreased with decreasing heart rate.

According to another preferred embodiment, the pump output of the pump is varied over a heartbeat cycle, such that a maximum pump output is reached during the systolic period, wherein a lower output is adjusted in order to augment the pressure during diastole when needed to facilitate coronary inflow. Preferably, a second sensor is needed to control the driving speed of the pump rotor to avoid cavitation within the heart, so that the pump accelerates only the equivalent volume portion needed in order to achieve normal ventricular ejection.

Alternatively or additionally, the control unit may comprise at least a further sensor for sensing a blood pressure, a cardiac output, a blood flow velocity, a derivative of the blood pressure and/or a pulse wave velocity and is configured to control the rotational speed of the pump rotor as a function of the signals derived from the further sensor. The blood pressure sensor may preferably be configured as a noninvasive blood pressure measuring device, in particular as a device operating according to continuous noninvasive techniques. The pulse wave velocity is preferably measured by a method for continuous pulse wave monitoring, such as identifying a time difference between a signal derived from the ECG and the corresponding signal measured at the patient's arm or other extremity by a non-invasive blood pressure measuring method.

Preferably, the control unit comprises a memory for storing at least one characteristic curve representing a set value for a blood pressure as a function of the heart rate. The control unit may in this case be configured to calculate a pressure difference between a blood pressure derived from the further sensor and a set value for the blood pressure derived from the characteristic curve and to control the rotational speed of the pump rotor as a function of said pressure difference.

Adapting the activation time period of the pump may be used in order to adjust the ejection time of the diseased heart to that of a healthy heart. This may alter the ejection and heart rate relationship according to the values registered by the further sensor(s).

As mentioned above, the further sensor may be configured to sense the cardiac output. In order to sense the cardiac output, the further sensor may be configured to measure the volume of the heart cavity, such as a sensor arranged for measuring the impedance across the heart. In particular, the ratio of the diastolic volume of the heart to the systolic volume of the heart per heartbeat or unit of time may be used in order to calculate cardiac output. The control unit may use the data representing cardiac output as sensed by the further sensor in order to adapt the rotational speed of the pump rotor in a close loop control. In particular, the control unit may be configured to control the rotational speed of the pump rotor such that the pump output is increased at a lower cardiac output rate measured by the further sensor, and is reduced at correspondingly higher measured values. The pump output of the pump is thus controlled primarily such that overall cardiac output rate which corresponds to a healthy heart is achieved. Further details for controlling the pump so as to compensate for a reduced cardiac output are described in U.S. Pat. No. 6,506,146.

Further, the control unit may preferably comprise or be connected to an activity sensor that measures the patient's type of activity, such as walking, sleeping, running etc. The activity sensor's signals may be used by the control unit to control the rotational speed of the pump rotor and/or the activation time period of the pump as a function of said signals.

Preferably, the energy demand, in particular the current draw, of the pump is monitored. The energy demand is indicative of the viscosity of the blood to be pumped and therefore allows monitoring the thrombus formation within the pump. Preferably, an alarm is set at a certain progressive increase in energy demand.

As mentioned above, the control unit of the assist device is preferably configured to alternately activate (i.e. turn on and turn off) the pump in order to produce periodic variations of the blood flow within the pump housing and by varying the rotor speed to adapt to requirements of global hemodynamics in a closed loop routine. In order to synchronize the flow pulses produced by the pump with the heartbeat, a heartbeat sensor, such as an ECG (electrocardiography) is provided in order to detect an R wave or an R wave interval. Preferably, the control unit controls the pump such that each R wave triggers the operation of the pump for a minimum runtime of 250 milliseconds. The maximum runtime of the pump is selected such that the pump is switched off before the occurrence of the next R wave. Normally, the pump produces a flow pulse at each heartbeat. However, in case of a high heart rate, the control unit may skip every second heartbeat and produce an assisted flow pulse only every other heartbeat, in order not to go below the minimum runtime of 250 milliseconds. In this way, one flow pulse produced by the pump is superposed on two heartbeats. Alternatively the periodic run time is overruling the first sensor (such as, e.g., ECG) by monitoring second and third sensors, thus producing longer periods as ejection times in normal ventricles.

The assist device comprises energy storage, such as a percutaneous rechargeable battery, that energizes the electric motor of the pump as well as the control unit. Preferably, the rechargeable battery is configured to be charged by near field energy transmission. During normal operation energy is transferred to the implanted system, including the pump motor and the control unit by induction via the skin. At the same time, the implanted rechargeable battery is loaded. When the external energy source is decoupled, the energy supply for the electric motor is automatically switched to the implanted battery. In another embodiment an implantable dynamo is provided, which can be rotated by means of an outside magnet to fill the capacity of the implanted battery during the operation of the pump.

According to a further aspect the invention refers to a method for assisting blood flow in the cardiovascular system of a human, in particular for increasing the cardiac output of a human. The method comprises placing a pump inside the left ventricle of a human heart, the pump sucking in blood within the left ventricle and ejecting blood within the left ventricle thereby producing a blood flow directed to the aortic valve entraining blood volume from distal and outside of the device. Preferably, the pump sucks in the blood from the apex region of the left ventricle, in particular from a region near the apex in which the blood coming into the left ventricle via the mitral valve swirls in a vortex.

Preferably, the method comprises producing a pulsatile blood flow that is synchronized with the heartbeat. In particular, the pump flow is produced during the systole of the heart, while no blood flow is produced during the diastole.

Preferably the method further comprises driving the pump from outside the heart, in particular by using an electric or pneumatic motor that is arranged outside the heart and coupled to the pump by a coupling traversing the cardiac wall, in particular by a contact-free coupling. Preferably, a magnetic coupling is used as said contact-free coupling. Preferably, the coupling traverses the cardiac wall in the region of the apex of the heart.

Alternatively, the rotary drive for driving the pump rotor may also be arranged within the heart. Preferably, the rotary drive comprises a hollow stator with the blood driving impeller being arranged as a rotor within the stator and supported by electromagnetic forces.

According to a further aspect the invention refers to a method for placing a ventricular assist device inside a human heart, which comprises the following steps:

exposing the heart via a small left thoracotomy (the size of the thoracotomy is similar to that of a transcatheter aortic valve implantation, TAVI), exposing the left ventricle within the pericardial cradle thereby allowing a view to the apical region, placing a guide wire via the left ventricle into the aorta and advancing the guide wire into the descending aorta, advancing a dilatator via the apex into the left ventricular cavity and advancing the same along the guide wire into the aorta, cutting a hole into the cardiac wall in the region of the apex of the heart, advancing an expandable mounting ring around the dilatator through the hole and expanding it radially within the left ventricle, placing a second mounting ring at the outside of the heart vis-a-vis the first mounting ring and puncturing the myocardium with needles arranged on the second mounting ring, covering the second mounting ring with a hemostyptic and hemostatic material to prevent oozing of blood, pressing the first mounting ring against the second mounting and squeezing the rim of the hole in the cardiac wall between both rings, removing the dilatator, advancing the pump via the guide wire and positioning the pump within the mounting rings, preferably by use of a rapid closure system.

Preferably, the nozzle's flexible part is positioned towards the outflow tract allowing optimal flow into the aortic valve and is then fixed.

Further, if as a result of a reverse remodeling occurring within the heart the flexible part of the pump is not oriented towards the aorta any more, the flexible part is repositioned, which may be achieved by percutaneous activation.

DETAILED DESCRIPTION

Aspects of the present invention are disclosed in the following description and related figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention.

It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Figure 2A:
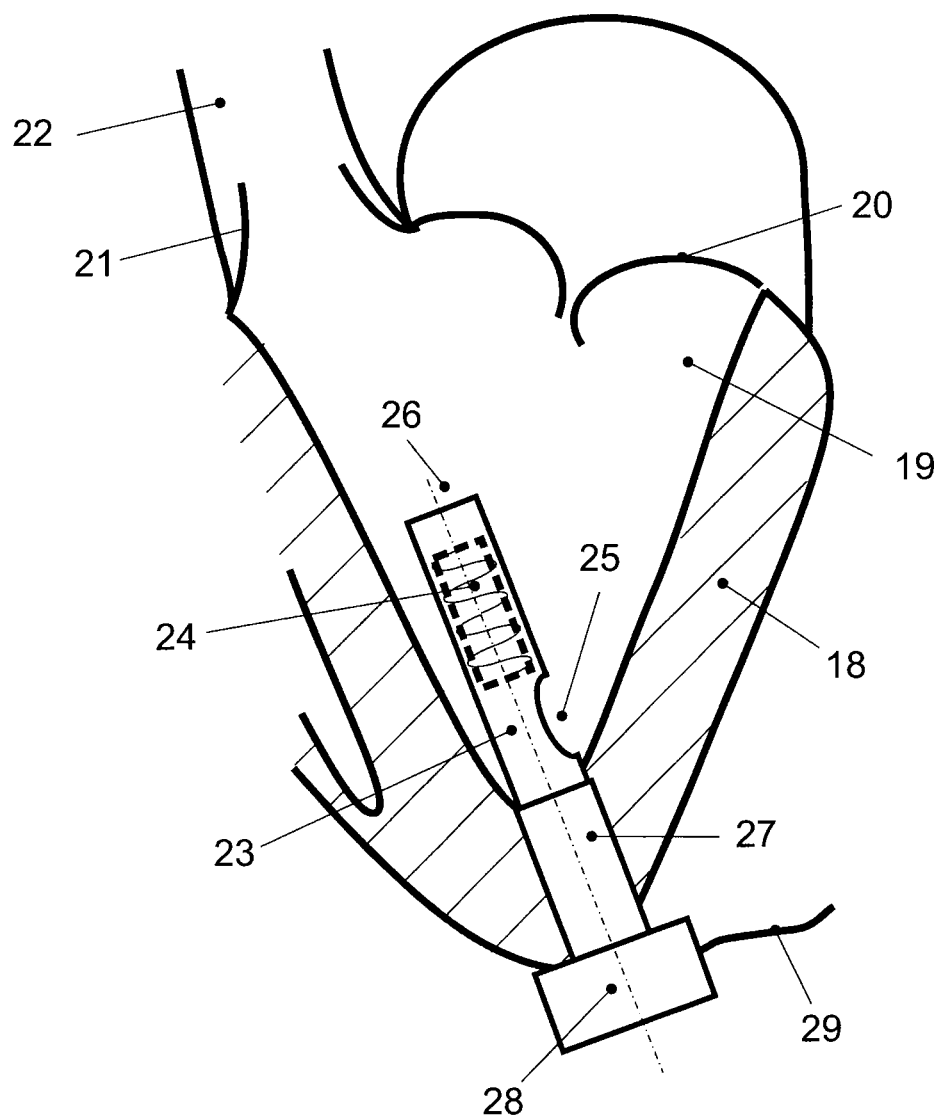
Figure 2B:
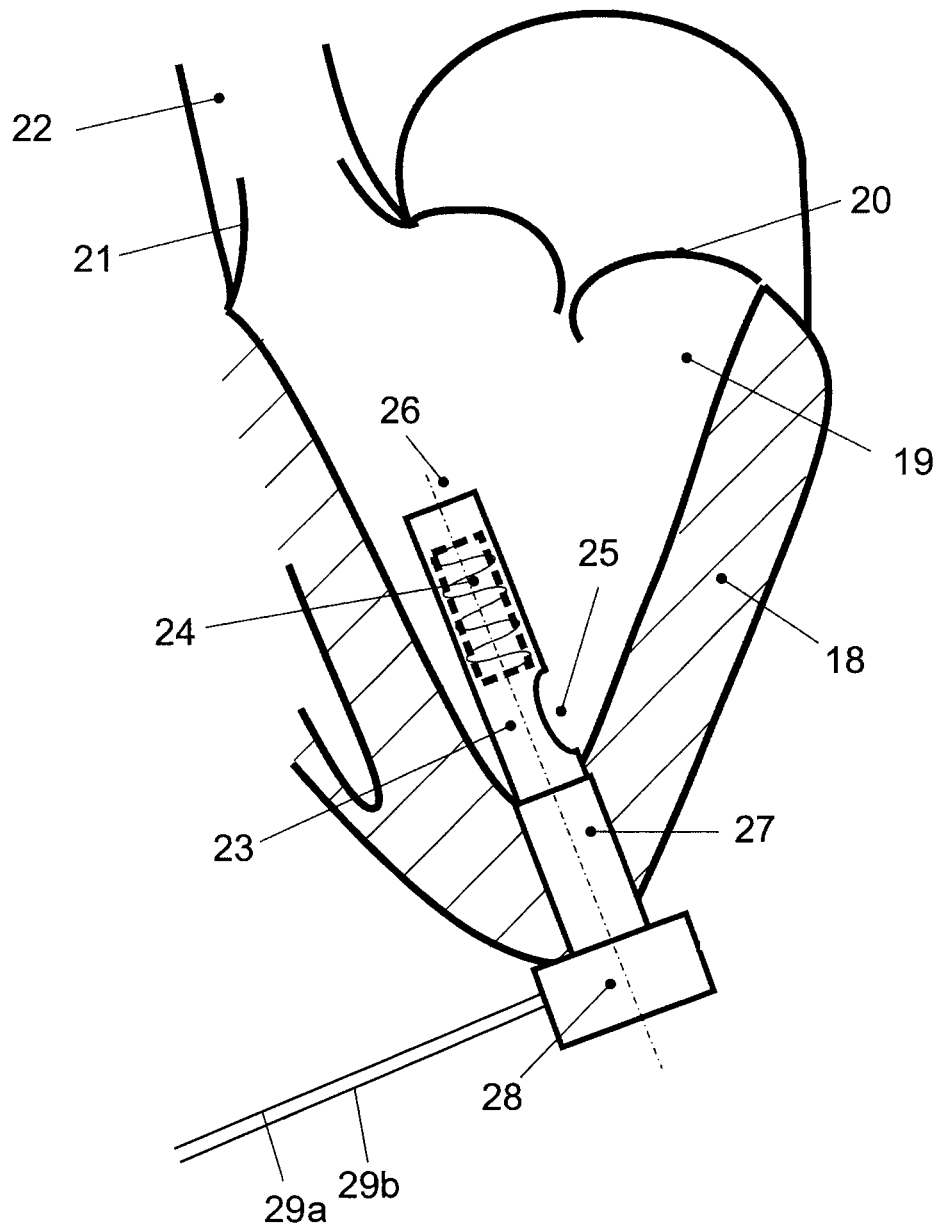
Figure 3:
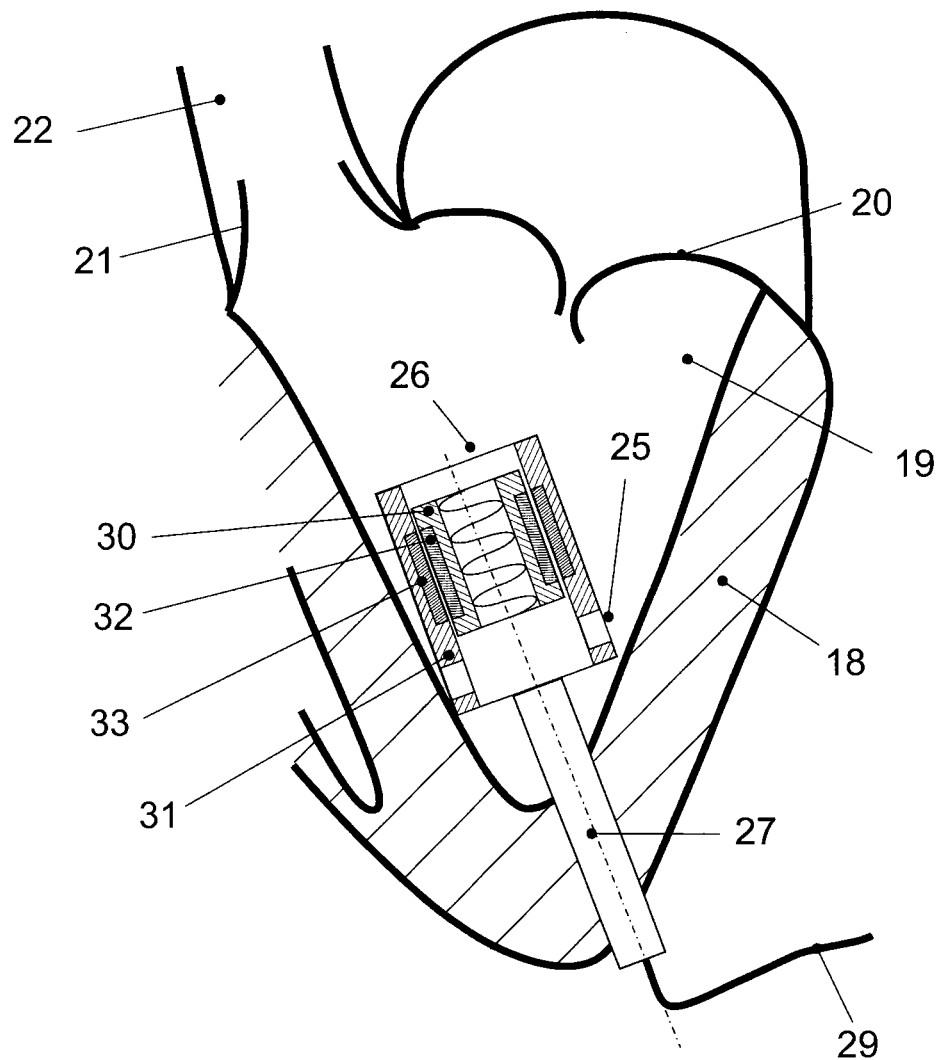
Figure 4:
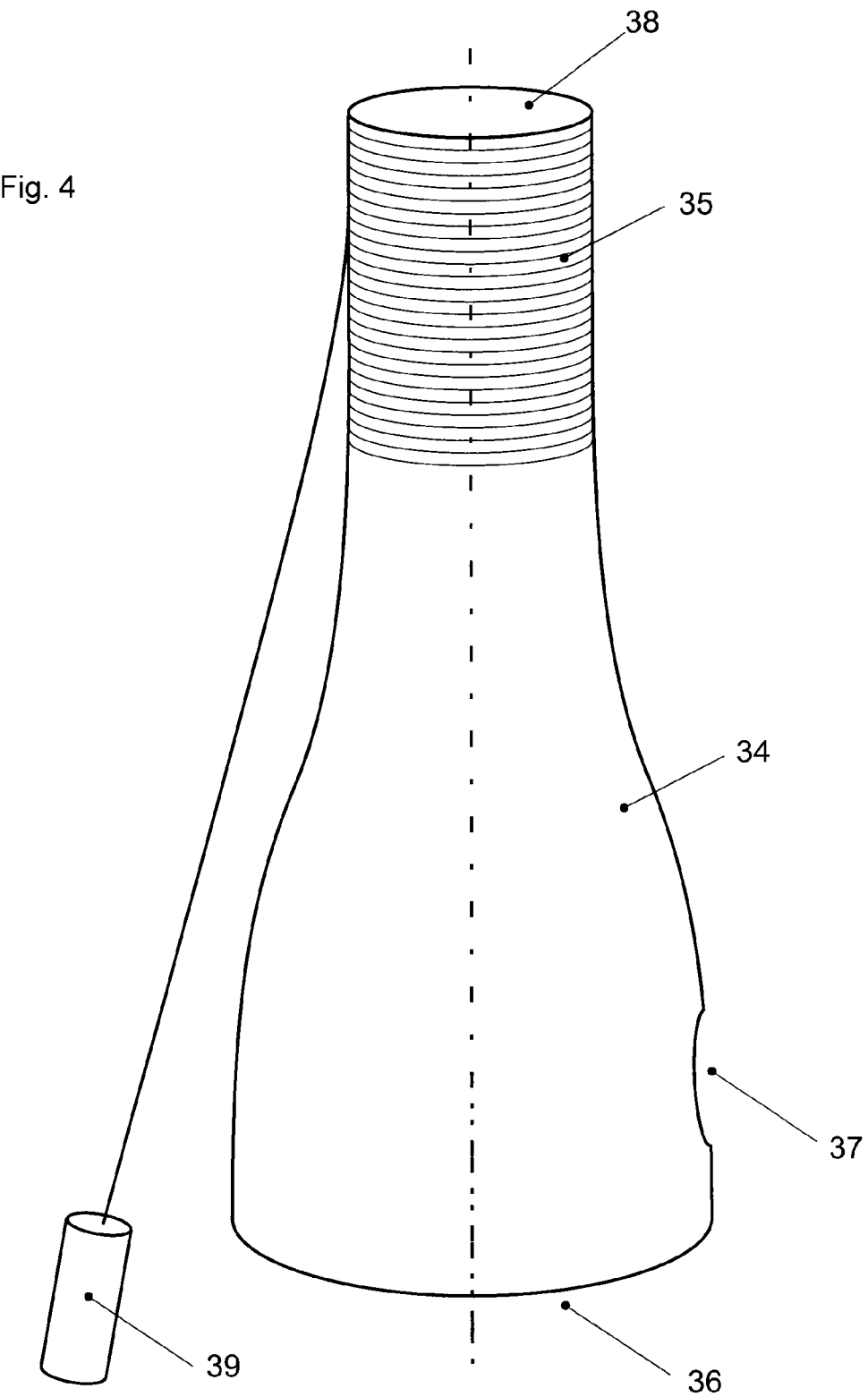
Figure 5:
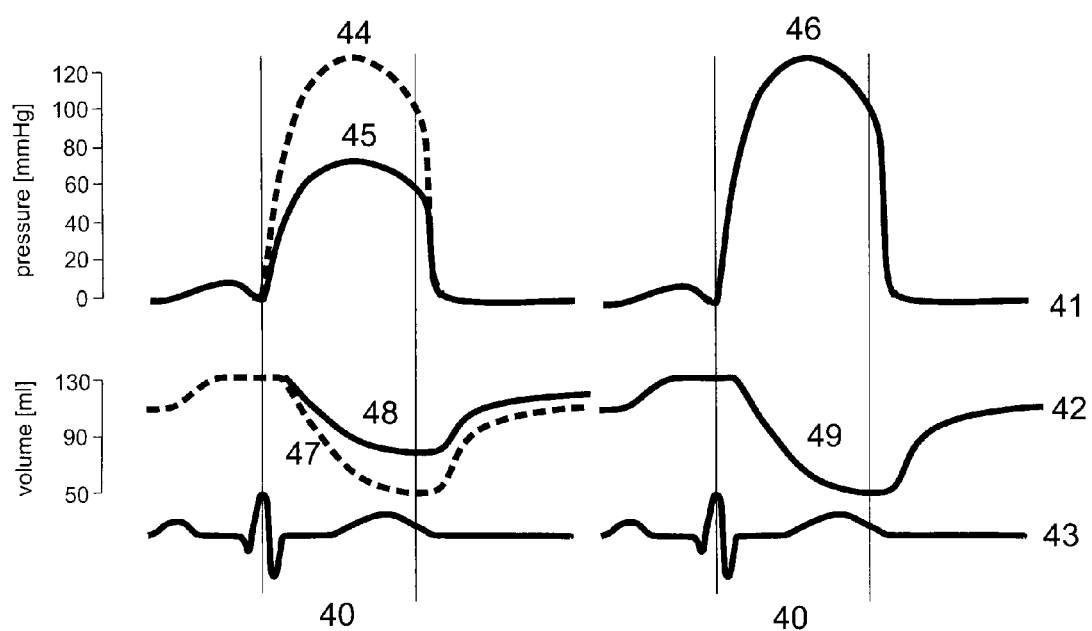
Figure 6A:
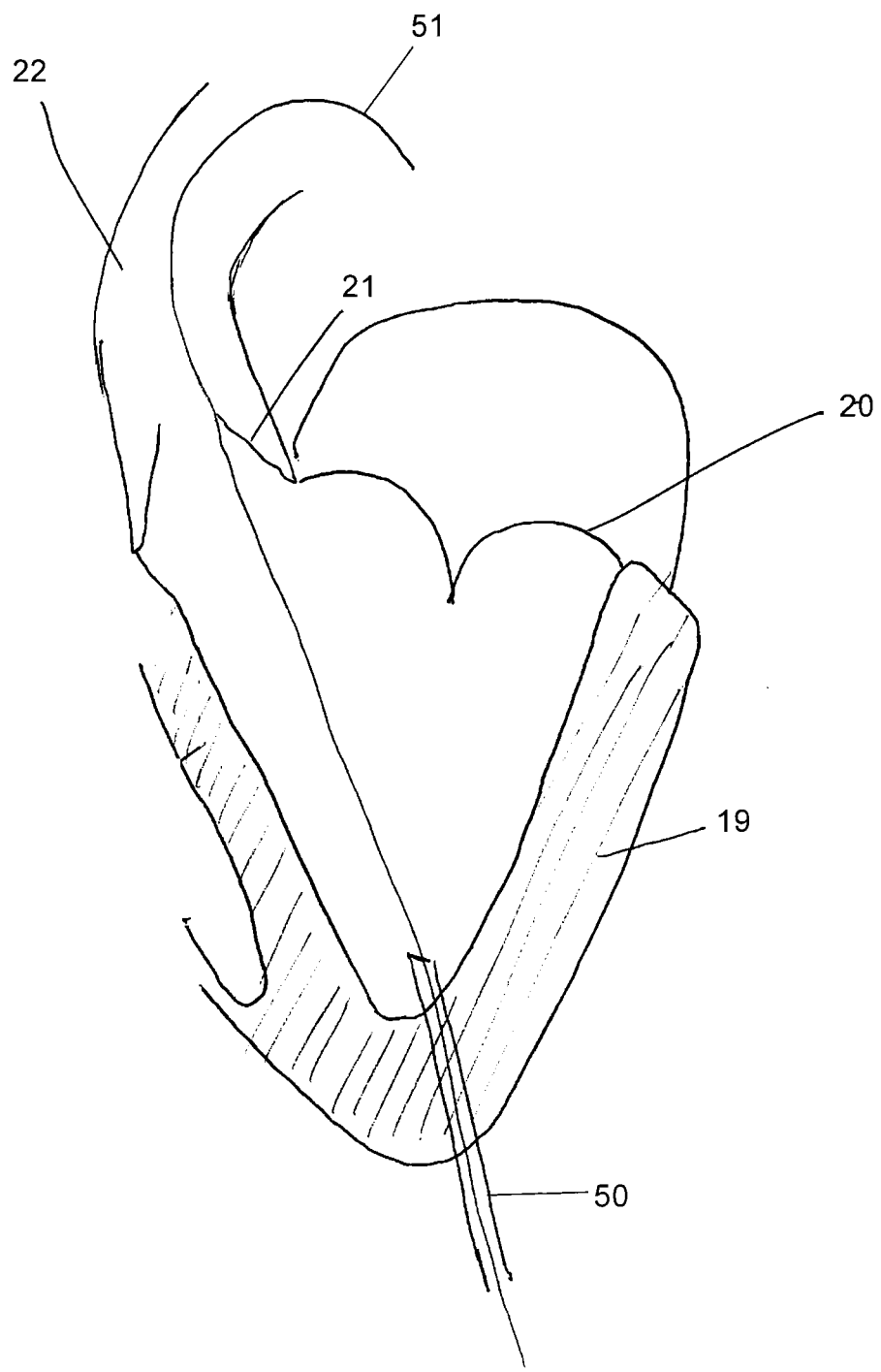
Figure 6B:
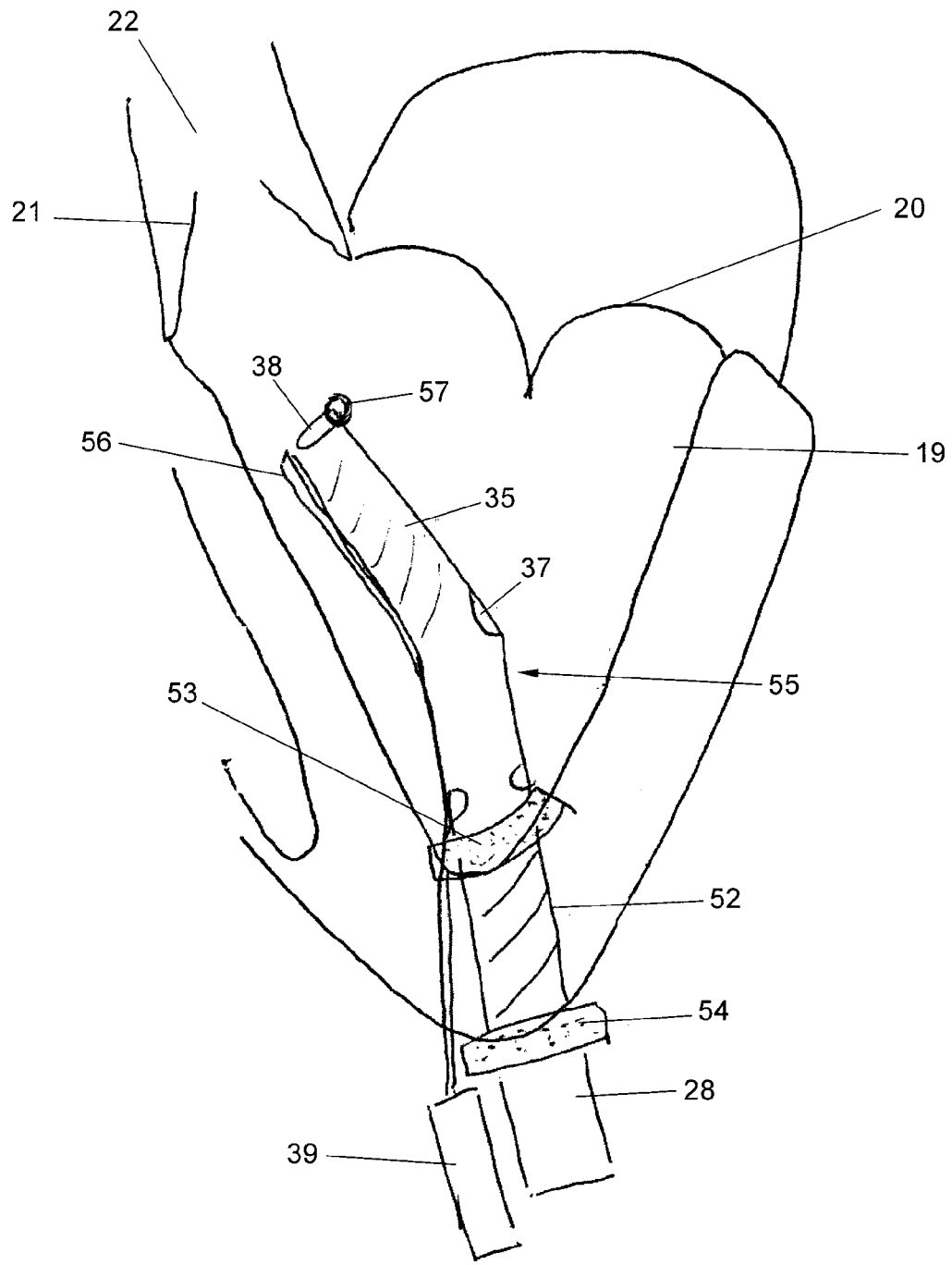

FIG. 1 is a schematic illustration of an assist device of the instant invention, FIG. 2a is a schematic illustration of a human heart with an assist device according to FIG. 1 being implanted and driven by an electric motor, FIG. 2b is an illustration according to FIG. 2a with the assist device being driven by a pneumatic drive, FIG. 3 is schematic illustration of a human heart with an alternative embodiment of the assist device being implanted, FIG. 4 is a schematic illustration of an adjustable outflow end region of a pump, FIG. 5 is a schematic illustration of a ECG signal, a sensor signal representing the ventricular volume and a sensor signal representing a ventricular pressure of a human heart, and FIGS. 6a and 6b show the implantation of the inventive assist device.

In FIG. 1 is a schematic illustration of an assist device of the instant invention. The assist device comprises a pump with a tubular housing 1 and a shaft 2. The shaft 2 is held in a rotational manner in a first axial bearing 3 and a second axial bearing 6. Further, the shaft is guided in a first radial bearing 4 and a second radial bearing 5. Wash borings for the bearings are denoted by 7.

The tubular housing 1 comprises an inlet opening 8 for sucking in blood form the left ventricle of a human heart. The inlet opening is configured so that blood flows into the tubular housing in a substantially radial direction. In the inside of the tubular housing 1 an axial rotor 9 is arranged in a rotatable manner and mounted to the drive shaft 2. When driven to rotation, the rotor 9 ejects blood via the outlet opening 10 into the left ventricle. The pump is mounted to the cardiac wall of the heart such that the flow leaving the pump via the outlet opening 10 is directed to the aortic valve. In order to adjust the flow direction, a tip portion 11 of the tubular housing is configured to be flexible or bendable. Further, the inner circumference of the tip portion 11 of the tubular housing 1 tapers so as to form a nozzle together with the central tip portion 12.

Preferably, the tip portion 11 of the tubular housing has at least one radial inlet opening schematically illustrated by arrow 13 so as to have additional blood sucked into the pump by the entraining action of the axial blood flowing in the tubular housing according to the injector principle.

Further, the tip portion 11 may have a beveled outlet opening 10 so as to obtain an end face that is inclined relative to the axis of the pump. The inclined end face is schematically denoted with dotted line 16.

The flow direction of blood located outside of the pump housing that is entrained by the effect of the pump is denoted by 17.

A first coupling element 14 of a magnetic coupling is fixed to the shaft 2. The first coupling element 14 cooperates with a second coupling element (not shown) in a non-contact manner. The first and the second coupling elements form a magnetic coupling. The second coupling element is connected to an electric or pneumatic motor, wherein the magnetic coupling transmits a rotational movement of the motor to the shaft 2. The cardiac wall is schematically denoted by 15. Thus, the electric or pneumatic motor is arranged outside of the heart.

FIGS. 2a and 2b are schematic illustrations of a human heart with an assist device according to FIG. 1 being implanted. The heart comprises a heart muscle 18, a left ventricle 19, a mitral valve 20, an aortic valve 21 and an aorta 22. The pump comprises a housing 23, a rotor 24, an inlet 25, an outlet 26, an anchor element 27, a drive (electric motor or pneumatic motor) 28, an energy supply line 29 (an electric wire in case of an electric motor, see FIG. 2a, or a catheter for gas supply in case of a pneumatic motor having a gas supply line 29a and a return line 29b, see FIG. 2b). In case of a pneumatic drive the motor 28 is configured as a turbine driven by the gas supplied through gas supply line 29a. The pump is oriented such that the outflow is directed to the aortic valve 21 and the aorta 22.

FIG. 3 shows an alternative embodiment, in which the electric motor for driving the pump rotor is arranged within the ventricle of the heart. The pump comprises a hollow rotor 30, a stator 31, rotor magnetic part 32 and stator magnetic part 33.

FIG. 4 is a schematic illustration of an adjustable outflow end region of the pump. The outflow end region comprises or is configured as a nozzle 34. Further, the outflow end region comprises an adjustable segment 35, the orientation of which can be changed in order to adjust the outflow direction of the blood pumped by the pump. The end region may comprise, in addition to the blood inlet 8 of the pump as shown in FIG. 1, an additional blood inlet 37 for entraining blood volume distal to the impeller. Further, a blood outlet 38 is provided. The adjustable segment 35 cooperates with an actor 39, such as an electric motor in order to adjust the outflow direction of blood. The adjustable segment 35 may be configured as a flexible or bendable end region of the pump housing. The actor 39 may be controlled by a percutaneous or internal flow signal. For example, an ultrasound flow sensor may be mounted on the adjustable segment to allow a periodic measurement of blood flow in the vicinity of the outlet 38 to automatically adjust the orientation of the orifice toward the aortic valve.

FIG. 5 shows the ECG signal, the ventricular volume of the left ventricle 19 and the ventricular pressure in the left ventricle 19 as a function of time, wherein the time period corresponding to the systole is denoted by 40. The ventricular pressure is denoted by 41, the ventricular volume is denoted by 42 and the electrocardiogram signal is denoted by 43. In a healthy heart, the average ventricular pressure during systole should be as denoted by 44. In contrast, a weakened, unassisted heart usually has a ventricular and aortic pressure during systole as shown at 45. Further, in a healthy heart the average ventricular volume during systole usually is as shown at 47, whereas the ventricular volume during systole for a weakened, unassisted heart is denoted by 48.

With the use of a ventricular assist device according to the instant invention the ventricular pressure of a weakened heart can be raised to normal levels as denoted by 46 during systole and the ventricular volume can be lowered to the level of a healthy heart as denoted by 49.

FIGS. 6a and 6b show the implantation of the inventive assist device. First, the ventricle 19 is punctured by a needle 50 and a guide wire 51 is advanced into the aorta 22 (FIG. 6a). Thereafter a knife with cross blades enlarges a hole dilating a port 52 in the ventricular wall and an expandable inner ring 53 is arranged to lie against the inner wall of the ventricle in a manner surrounding the port 52. A hemostyptic outer ring 54 is arranged at the outer wall of the ventricle in a manner surrounding the port 52, whereby the inner ring 53 is fixed against the outer ring 54 thereby allowing bloodless fixation of the pump 55. The adjustable segment 35 of the pump is attached to a steering element 56, which is able to adjust the outflow orientation of the pump so as to direct the outflow towards the aorta 22. The steering element 56 is actuated by a motor 39, which is controlled by an implanted ultrasound sensor 57 by means of a closed loop control or by a percutaneous signal. The electric or pneumatic drive of the pump is denoted by 28.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

The invention claimed is:

1. A ventricular assist device for intraventricular placement inside a human heart comprising:
   an anchor element configured to be mounted to the heart in the region of the apex,
   a pump connected to the anchor element and comprising a tubular housing having an inlet and an outlet and further comprising drive for driving a rotor arranged within the housing,
   a control unit connected with the drive for controlling the pump, said control unit comprising a first sensor for sensing a heartbeat of the heart and configured to control the pump to be driven in a pulsatile manner in synchronization with the heart beats,
   wherein an end region of the pump housing is percutaneously adjustable to adjust the flow direction of blood exiting the pump towards the aortic valve, the adjustable end region comprises an ultrasound sensor for sensing a blood flow, and a sensor signal being used for periodically adjusting the orientation of the adjustable end region of the pump housing to be oriented towards the aortic valve.

2. The assist device of claim 1, wherein the inlet and the outlet of the housing are configured for arrangement within the ventricle.

3. The assist device of claim 1, wherein the pump comprises a magnetic coupling for coupling the drive to the rotor.

4. The assist device of claim 1, wherein the drive is at least partially arranged proximally of the anchor element so as to be placed at least partially outside of the heart when in use.

5. The assist device of claim 1, wherein the control unit is configured to control the rotational speed of the pump rotor as a function of heart rate signals derived from the first sensor.

6. The assist device of claim 1, wherein the control unit comprises at least a further sensor for sensing a blood pressure, a cardiac output, a blood flow velocity, a derivative of the blood pressure and/or a pulse wave velocity and is configured to control the rotational speed of the pump rotor as a function of the signals derived from the further sensor.

7. The assist device of claim 1, wherein the control unit comprises a memory for storing at least one characteristic curve representing a set value for a blood pressure as a function of the heart rate.

8. The assist device of claim 7, wherein the control unit is configured to calculate a pressure difference of a blood pressure derived from a further sensor and a set value for the blood pressure derived from the characteristic curve and to control the rotational speed of the pump rotor as a function of said pressure difference.

9. The assist device of claim 1, wherein a flow cross-section of the pump continuously decreases in a flow direction at the outflow end of the pump housing so as to form a nozzle able to direct the flow towards the aortic valve and entraining surrounding blood.

10. The assist device of claim 1, wherein the adjustable end region cooperates with fixing means to fix the end region in the adjusted position.

* * * * *